United States Patent [19]
Crock

[11] Patent Number: 6,016,450
[45] Date of Patent: Jan. 18, 2000

[54] METHOD AND APPARATUS FOR STIMULATING THE HEALING OF LIVING TISSUE USING AURA THERAPY

[76] Inventor: Leander Crock, 515 West St., Caldwell, Ohio 43724

[21] Appl. No.: 09/109,397

[22] Filed: Jul. 2, 1998

[51] Int. Cl.[7] .................................................. A61N 1/00
[52] U.S. Cl. .................................. 607/50; 607/2; 607/75
[58] Field of Search .............................. 607/1, 2, 45, 50, 607/74, 75; 600/407, 411; 396/14, 661; 250/326; 361/232

[56] References Cited

U.S. PATENT DOCUMENTS

| | | | |
|---|---|---|---|
| 3,678,337 | 7/1972 | Grauvogel | 317/4 |
| 4,222,658 | 9/1980 | Mandel | 354/354 |
| 4,386,834 | 6/1983 | Toolan | 354/3 |
| 4,611,599 | 9/1986 | Bentall et al. | 607/2 |
| 4,679,924 | 7/1987 | Wamsley | 354/3 |
| 5,899,922 | 5/1999 | Loos | 607/2 |

*Primary Examiner*—Jeffrey R. Jastrzab
*Attorney, Agent, or Firm*—Joseph H. Taddeo

[57] ABSTRACT

A therapeutic method and apparatus to induce the healing of tissue cells by an electrical stimulus to a tissue area with the problematic condition by the application of low density charges of alternate polarities. The apparatus performs the therapeutic function by alternately charging and discharging the cells in 15 minute intervals over periods time from 1 to 12 hours.

9 Claims, 3 Drawing Sheets

METHOD AND APPARATUS FOR STIMULATING THE HEALING OF LIVING TISSUE USING AURA THERAPY

FIELD OF INVENTION

The present invention relates to therapeutic methods and apparatuses, and more particularly to a method and device to stimulate the healing of living tissue by repairing damaged aurae.

An aura is an invisible envelope of vital energy, which apparently radiates from everything in nature: minerals, plants, animals, and humans. It is not visible to normal vision, but may be seen by those who are sensitive to these emanations as a halo of light. It often appears as a multi-colored mist that fades off into space with no definite boundary, and having sparks, rays, and streamers.

Much of what is purported to be known about the aura is based on paranormal experiences where no scientific evidence has been found to prove its existence. The body does, however, have a magnetic field, a biofield, as it is called, but it is far too weak to account for a light-emitting aura. Even if the field were many times stronger, it still would be insufficient to emit light. It has been theorized that the aura might actually be a form of light that emanates at frequencies beyond the normal range of vision, caused by some yet-to-be-discovered light emitting substance embedded in living organisms. Another theory suggests that those who are sensitive to these emanations, who say they see the aura, may in fact see the magnetic field, which may register as light, perhaps because of some sort of sensitive magnetic detector in the brain.

BACKGROUND OF THE INVENTION

The emanation of vital energy from life forms is believed to have originated in ancient times, and appears in the writings and art of Egypt, India, Greece, and Rome. In the sixteenth century, Paracelsus was one of the first Western scholars to expound upon the astral body, which he described as a "fiery globe." In the eighteenth century, the clairvoyant Emanuel Swedenborg said in his Spiritual Diary that "there is a spiritual sphere surrounding every one, as well as a natural and corporal one."

The scientific study of the aura began in the late eighteenth century, when Franz Anton Mesmer put forth the theory of "animal magnetism," an electromagnetic force that could be transmitted from one person to another and effect healing. In 1845, Baron Karl von Reichenbach, a German chemist, announced the discovery of the "odic force" energy. Reich-enbach's clairvoyant test subjects sat in darkened rooms and saw flame-like energy radiating from fingertips, animals, plants, magnets, and certain crystals. The subjects described seeing flames of red, orange, green, and violet, which alternately appeared and disappeared; a violet-red, which disappeared in a smokelike vapor; and intermingled in streamers, sparks and stars among all colors.

Shortly before World War I, Dr. Walter J. Kilner, who was in charge of electrotherapy at St. Thomas's Hospital in London, discovered that an apparent human aura could be made visible if viewed through an apparatus containing a coal-tar dye called dicyanin, which made ultraviolet light visible.

Kilner saw the aura as a faint haze, which sometimes could be separated into two or three portions. It enveloped the whole body. Men in good health all showed the same aura characteristics, women, however, varied. In childhood their auras appeared the same as males, but by adulthood were more developed and more refined in texture, according to Kilner.

He divided the aura into three parts: (1) the etheric double, a transparent dark space, narrow and often obliterated by the second band; (2) the inner aura, fairly constant in size and the densest portion; and (3) the outer aura, varied in size, which often appears blended into the inner aura. He also observed rays emanating from the body in healthy people. Kilner noticed that the aura reflected the state of health, and by 1919, formulated a method of auric diagnosis of illness. In some cases the aura was affected only locally, while in other illnesses, the entire aura was affected; as the patient recovered, so did the aura. Kilner also noticed that weak, depleted auras drains the auric energy of healthy, vigorous auras around them.

Kilner published the results of his early research in The *Human Aura* in 1911. It was greeted with a great deal of skepticism, but he continued his experiments, attracting the interest of Sir Oliver Lodge. Kilner's work was interrupted by World War I. In 1920, he published a revised edition of his book, which was sympathetically reviewed.

Those who are sensitive to emanations from the aura, see the aura as emanating from and interpenetrating the human body. Health and emotion show in various colors, energy patterns or breaks, and clear and cloudy spots.

Physical health appears to be related to the part of the aura that is closest to the body, often called the vital body or etheric body. It is said that illness manifests first in the etheric body, sometimes months or years before its physical symptoms manifest. Except for the etheric body, which appears to directly affect health, the composition of the aura is the subject of conflicting opinions. No two observers see exactly the same aura. Some say they see the entire aura, divided into different layers or bodies, while others say they see only parts of the aura.

Interpretations of the colors seen in the aura vary considerably. There is little agreement by observations made by those sensitive to emanations from the aura, as to what is seen when they view an aura that is exactly same. Some say they see the entire aura, divided into different layers or bodies, while others say they see only parts of the aura. Further, it appears that the aura fluctuates constantly, and that various colors reflect the fluctuations.

To reduce the variability in interpretation and improve the repeatability, Semyon Davidovich Kirlian, a Russian electrician, began work in 1939 that led to the development of techniques purported to record the aura on film.

Kirlian Photography

Kirlian photography is a technique for photographing objects in the presence of a high frequency, high voltage, low current electrical field. The photographs of which show glowing, multicolored emanations are said to be auras or biofields. Some researchers say it reveals a physical form of psychic energy. Others believe that it reveals the etheric body; that is, one of the layers of the aura believed to permeate all living things and, that an understanding of this energy will lead to greater insights into medicine, psychology and healing. Critics say the technique shows nothing more than a discharge of electricity, which can be produced under certain conditions.

Prior to Kirlian's work, the process of photographing objects in electrical fields was generally known as "electrography" or "electrographic photography." Little value was seen in the process, which received scant attention from researchers. Electrographic photographs date to as early as 1898, when another Russian, Yakov Narkevich Yokdo (also given as Todko), displayed his work at a photographic exhibition. Research was published by a Czech, B. Navratil, in the early 1900s. In 1939, two Czech researchers, S. Prat and J. Schlemmer, published photographs of leaves showing coronas.

Kirlian used his own hand for his first experiment, and photographed a strange glow radiating from the fingertips. He and his wife, Valentina, a biologist, experimented with photographing both live and inanimate subjects. In the ensuing years, the couple refined their equipment and graduated from black-and-white to color photography.

The principle of Kirlian photography and all electrography is the corona discharge phenomenon, which occurs when an electrically grounded object discharges a corona between itself and an electrode generating the electrical field. The corona discharges are captured on film, appearing as coronas of light. These discharges can be affected by temperature, moisture, pressure, and other environmental factors. Various Kirlian techniques have been developed, but the most basic uses a Tesla coil connected to a metal plate. The process is similar to one that occurs in nature, when electrical conditions in the atmosphere produce luminescences and auras, such as St. Elmo's fire.

Kirlians' work was brought to the attention of the West in the 1960s. Response in the scientific community was mixed, but sufficient interest led to a gathering of interested scientists in Alma Ata in 1966. Biophysicist Viktor Adamenko theorized that the energy field was the "cold emission of electrons," and their patterns might suggest new information about the life processes of animate objects. Adamenko and other Soviet scientists discerned that biological energies of humans were brightest at the seven hundred points on the body that coincide with Chinese acupuncture points.

Kirlian photos are said to reveal health and emotion by changes in the brightness, colors, and patterns of the light. Experiments in the 1970s, conducted by Thelma Moss and Kendall Johnson at the University of California's Center for Health Sciences at Los Angeles, showed changes in a plant's glow when approached by a human hand and pricked. When part of a leaf was cut off, a glowing outline of the amputated portion still appeared on film. Moss, Kendall, and other researchers found that the glow around humans similarly reflected changes in emotional state.

Some Kirlian enthusiasts consider the phantom leaf phenomenon evidence for the existence of an etheric body. However, critics say the phenomenon disproves Kirlian photography altogether; Should the method truly have photographed a biofield, then the aura should disappear when an organism dies. The effect that is produced is solely by a high-voltage electric field breakdown of air molecules between two condenser plates.

Supporters nonetheless foresee applications of Kirlian photography in diagnostic medicine. Experiments using Kirlian photographs to detect cancer have been sporadically successful. Some researchers envision diagnostic systems that combine Kirlian photography with computerized tomography (CT) scanners (advanced versions of computerized axial tomography or CAT scanners, which utilize a thin beam of X-rays to photograph an object from 360 degrees) and magnetic resonance imaging (MRI). The latter technique uses no X-rays, but uses magnetic fields to produce images of body cells and water in tissues.

Chakras

Chakras are the vortices that penetrate the body and the body's aura, through which various energies, including the universal life force, are received, transformed, and distributed. Chakras are believed to play a vital role in physical, mental, and emotional health and in spiritual development. They are invisible to ordinary sight but may be perceived clairvoyantly or by use of aura photography. It is said of some people that they can activate the chakras to whirl faster and can direct the flow of energy through them.

Chakra is Sanskrit for "wheel." Chakras are said to be shaped like multicolored lotus petals or spoked wheels that whirl at various speeds as they process energy. There are differences between the two systems, and in various Western descriptions of the chakras.

There is no accepted scientific definite evidence that the chakras exist; until recently, they were dismissed by Western medicine. They have been increasingly acknowledged, along with the acupuncture, meridians and other Eastern Systems, in alternative treatments. Evidence for the existence of chakras, albeit controversial, has been presented by Hiroshi Motoyama of Japan, who hypothesized that an enlightened person could influence the chakras, and the energy output would be measurable. Using a lead-lined recording booth, Motoyama measured the energy field opposite various chakras which subjects claimed to have awakened, usually through years of meditation. He found that the energy levels at those areas were significantly greater than over the same areas of control subjects.

The health of chakras is diagnosed by clairvoyance or by energy scans. Clairvoyants say that health disturbances often manifest in the aura, and thus in the chakras, months and sometimes years before they manifest in the physical body.

BRIEF DISCUSSION OF THE PRIOR ART

The referenced prior art that follows, shows one disclosing an aura camera device, while others show low voltage treatment devices, some operating at various frequencies. In particular:

U.S. Pat. No. 3,774,620, granted Nov. 27, 1873, to A. Hansjurgens, discloses an electromedicinal apparatus for use in interference therapy. Treatment is produced by stimulation to the target area of a patient, through electrodes, each operating at different frequencies, set by varying current densities, whose frequency difference is in the low frequency range.

U.S. Pat. No. 4,471,787, granted Sep. 18, 1984, to R. H. C. Bentall, discloses a portable apparatus comprising a battery driven r.f. oscillator and an antenna which is flexible to overlie an area of tissue to be treated.

U.S. Pat. No. 5,132,714, granted Jul. 21, 1992, to S. W. Samon, discloses a portrait camera with an aura generating means for creating a photographic of a portrait subject and a visible aura image.

U.S. Pat. No. 5,133,352, granted Jul. 28, 1992, to P. H. Lathrop, et al., discloses an apparatus and method for treating infectious skin conditions, by the application of an electrical field and current to the affected area to activate a reaction at the cell level to combat the virus and disrupt its attack on a healthy cell structure. The apparatus consists of a low voltage, low direct current device. It is recommended that the infected skin area be stimulated, using the device, for a few seconds each hour.

U.S. Pat. No. 5,268,304, granted Dec. 14, 1993, to T. Matthews, discloses an electrotherapy apparatus having at least two electrodes to feed an oscillating current to selected areas on or beneath the epidermal or mucous surface remote from the treatment site. The feed electrodes operate at different frequencies so that the treatment site is stimulated by the beat frequency, which may be at 80 or 130 Hz.

The present invention differs from the aforementioned prior art in that the approach is not limited to the use of high frequency applications to effect a healing stimulus, but uses an application of a steady state charge that is intermittently reversed in a therapeutic manner.

Accordingly, it is therefore an object of the present invention to provide an apparatus to stimulate the healing of living tissue through the use of aura therapy.

These as well as other objects and advantages of the present invention will be better appreciated and understood upon reading the following detailed description of the presently preferred embodiment taking in conjunction with the accompanying drawing.

SUMMARY OF THE INVENTION

The general objective of the present invention is to provide a novel tool to aid in the determining the location of a malfunctioning area within the body. This is accomplished by using a means of photographing one's aura so that it remains as a permanent record, in such a manner, much like that of an X-ray. In addition, the present invention also provides for a novel apparatus to stimulate the therapeutic healing of the damaged living tissue.

The aura is a representation of one's life force energy, which is an electrical field that surrounds the body. When an aura photograph is taken, there are spots of light that show up in front of the body, which are the energy centers where the nerves come together. An aura camera records the energy density at these energy center locations because there is more energy radiated from these points.

When one's energy system becomes clogged, and part of the body stops functioning properly, it is not receiving the signals that it should and the aura will have a hole in it. Once the healing process is completed and the body healed, the aura becomes complete, where one once treated will feel good again.

The colors associated with one's aura show the condition of one's body and reveal the location of the problematic condition. The aura is given by our body's energy, which some clairvoyants see and the aura camera shows as colors. In other words, the human body's energy is visible; the colors depend on the speed. The slower the energy, the stronger the color will be. For example, the slowest vibration is red and the fastest white.

One can also combine the meaning of the aura colors with that of the chakra colors. Chakras are the energy centers in our body. If the energy is a certain color, it means that the attention is mainly centered in a certain part of the body. For example, if one vibrates in yellow, they are sensitive in the stomach area and the third chakra is open or opens up at this time; they may also be involved yellow themes like trying to be independent.

Just taking a nice aura photo is not enough, the interpretation of an aura photo is the most important. To read an aura photo you have to consider it's many different parts: the shape of the aura, the energy positions and the color of the aura.

Trained therapists can restore the electrical system of the body and open up the channels of energy that run through us. When part of our body becomes clogged or stagnant, it presents itself as pain in that area.

An individual's aura also contains information of one's personality. It consists of the electricity spent that one's body has used in order to function. Spent electricity cannot be stored in an individual and it cannot be discharged into the ground, so when it is discharged into the air, it is referred to as the aura.

BRIEF DESCRIPTION OF THE DRAWINGS

The present invention is schematically illustrated in the accompanying drawings that are attached herein.

DETAILED DESCRIPTION OF THE INVENTION

In the past, the observation of the aura was only seen by clairvoyants, those who are sensitive in viewing emanations from the aura. It is now believed that the acquired skill of viewing the human aura occurred best when the clairvoyant was having an episode of epilepsy, migraine or other types of neurological disorders.

A method of standardizing the viewing of the human aura was developed using Kirlian photography. Kirlian photography is a technique for photographing objects in the presence of a high frequency, high voltage, low current electrical field. The photographs of which show glowing, multicolored emanations are said to be auras or biofields.

The principle of Kirlian photography and all electrography is the corona discharge phenomenon, which occurs when an electrically grounded object discharges a corona between itself and an electrode generating the electrical field. When the corona discharges are captured on film, they appear as coronas of light.

Various Kirlian techniques have been developed, but the most basic uses a Tesla coil connected to a metal plate. The subject is typically in a darkened room, such a photographer's dark room, and a photographic film is placed adjacent or behind to the subject. The corona discharge produces illumination in the visible light spectrum that is captured on film.

The Tesla coil that is employed is an air-core transformer that is used as a source of high-frequency power, such as for use with x-ray tubes. It was invented by Nikola Tesla, a prominent Serbian-born American electrical engineer and physicist who discovered the principles of alternating current in 1881 and invented numerous devices and procedures that were seminal to the development of radio and the harnessing of electricity. He was a pioneer in high-tension electricity. His many discoveries and inventions were of great value to the development of radio transmission and to the field of electricity, including an arc-lighting system, the Tesla induction motor, the Tesla coil, and various generators and transformers.

Figure 2:
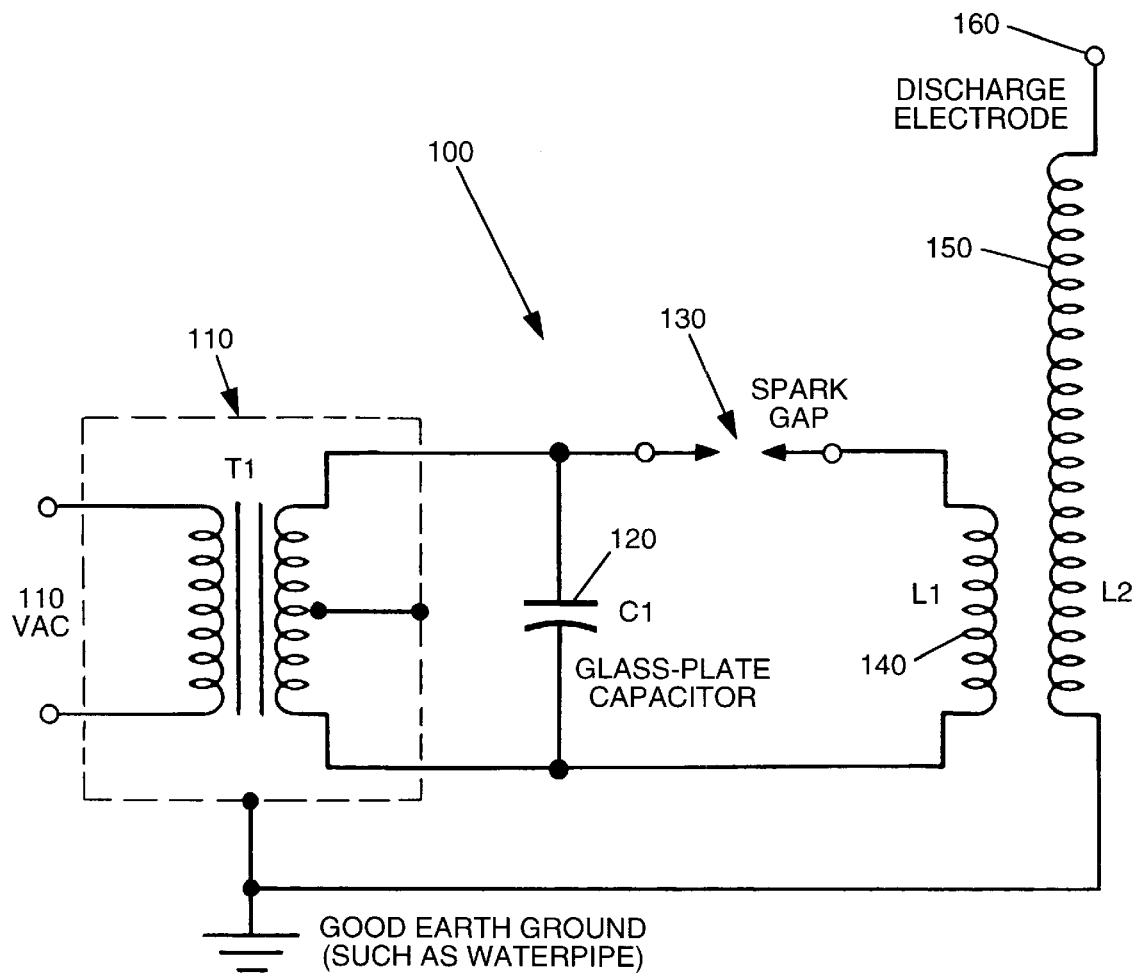
FIG. 2 is a prior art schematic drawing of the apparatus designed and used by Nikola Tesla for generating high frequency, high voltage, low current, having a visible corona discharge.

The Tesla coil 100 is best illustrated by referring to the schematic drawing of FIG. 2. An input transformer 110 steps the applied voltage from 110 VAC to approximately 17,000 VAC. Immediately connected across the secondary is a glass-plate capacitor 120. The capacitor serves as an energy storage device, charging up to the voltage of the secondary of step-up transformer 110. When the instantaneous voltage exceeds the breakdown voltage of the air spark gap 130, current flows through the primary coil 140 (L1) of the air core transformer 150. The discharging of capacitor is through the spark gap into the primary coil L1. The larger the capacitor, the greater the current flowing through L1. The resulting voltage appears across the secondary winding 150 (L2) of the air core transformer, which can range from 75,000 to 250,000 volts.

Discharges across the spark gap produces extremely jagged and random pulses of power that are extremely rich in r.f. harmonics. The output voltage is maximum when the primary winding and capacitor are tuned to the resonant frequency of the secondary coil co-acting with its distributed capacitance (not shown). The corona discharge is available at terminal 160, where it can be observed usually in the violet region.

The visible light spectrum ranges from 400 to 700 millimicrons. For example, the three primary colors differ in frequency; where red is between 610 and 700 millimicrons, green is between 500 to 570, and blue, between 450 and 500.

The visual effect that results is from the eye's ability to distinguish the different wavelengths or frequencies of light. The apparent color of an object depends on the wavelength of the light that it reflects. In white light, an opaque object that reflects all wavelengths appears white and one that absorbs all wavelengths appears black. Any three primary, or spectral, colors can be combined in various proportions to produce any other color sensation. Beams of light are combined "additively," and red, blue, and green are typically chosen as primaries.

Figure 3:
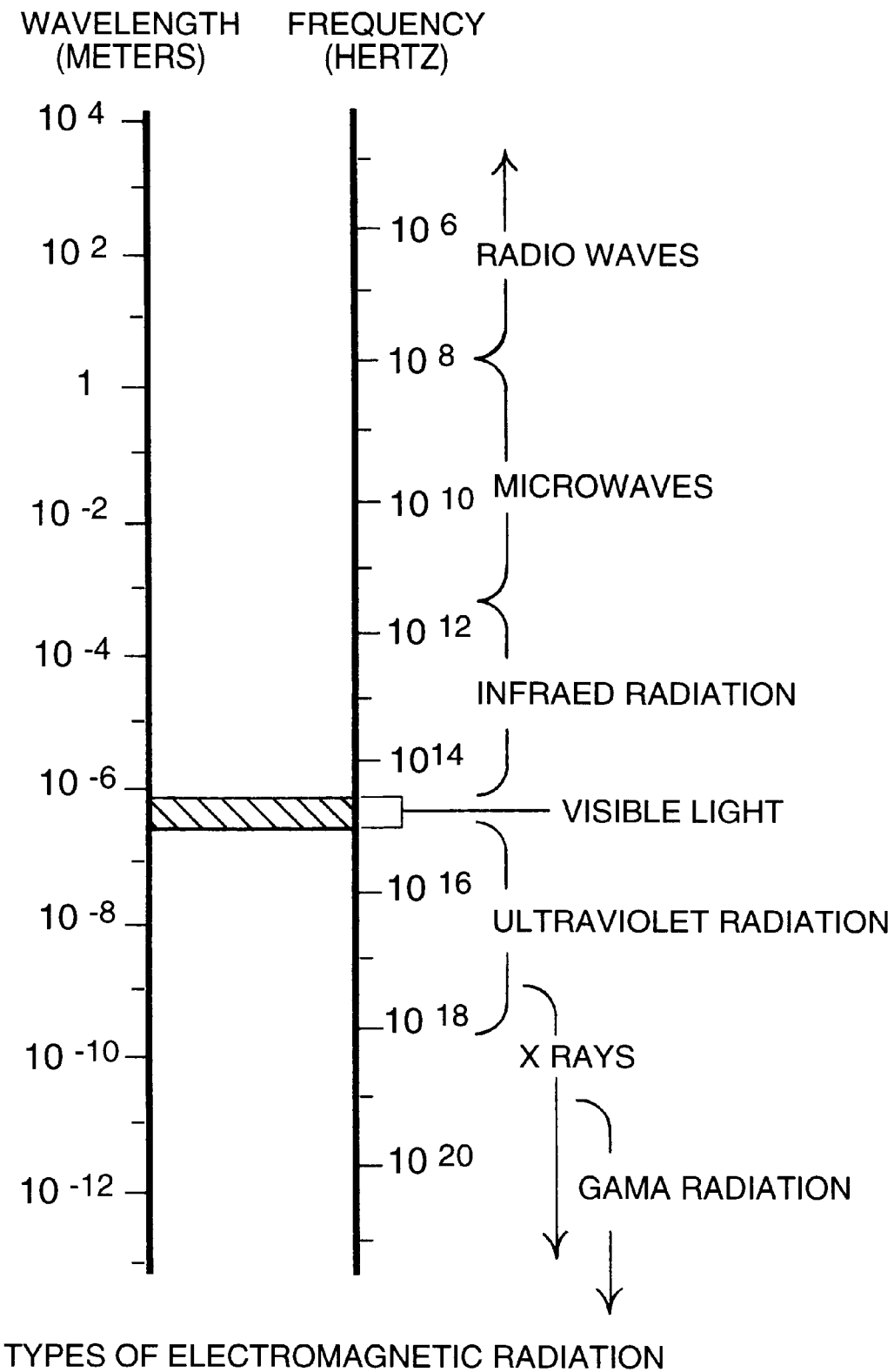
FIG. 3 is a graph illustrating the known range of frequencies for various types of electromagnetic radiation.

It is known that the aura cannot be viewed directly by most persons, except for those whose are sensitive to these emanations, such as clairvoyants. As shown in FIG. 3, there numerous electromagnetic radiation's that cannot be directly observed; radio waves require r.f. receivers to be detected, as do microwave sensors and infrared sensors.

Electromagnetic radiation is the result of the acceleration of a charged particle. It does not require a material medium, and can travel through a vacuum. In order of decreasing wavelength and increasing frequency, the various types of electromagnetic radiation are radio waves, microwaves, infrared radiation, visible light, ultraviolet radiation, x rays, and gamma radiation. The possible sources of electromagnetic radiation are directly related to wavelength; long radio waves are produced by large antennas such as those used by broadcasting stations; much shorter visible light waves are produced by the motions of charges within atoms; the shortest waves, those of gamma radiation, result from changes within the nucleus of the atom.

It is theorized that the wavelength of the aura may reside in the frequency domain within the gamma region or beyond. By using the Tesla coil in conjunction with the Kirlian photography, the harmonics generated by the Tesla coil combine in such a manner with one's aura to produce different frequencies that lie within the visible light spectrum, allowing the colored corona discharge to be photographed.

Once the colored photograph of the aura is produced, trained technicians can effectively determine the nature of a malfunction should one be present.

The present invention provides a novel tool to aid in the determining the location of a malfunctioning area within the body. This is accomplished by using a means of photographing one's aura so that it remains as a permanent record, in such a manner, much like that of an x-ray. In addition, the present invention also provides for a novel apparatus to stimulate the therapeutic healing of the damaged living tissue.

The aura, once detected, shows one's life force energy, which is an electrical field that surrounds the body. When an aura photograph is taken, there are spots of light that show up in front of the body, which are the energy centers where the nerves come together. An aura camera records the energy density at these energy center locations because there is more energy radiated from these points.

The colors associated with one's aura show the condition of one's body and reveal the location of the problematic condition. When the human body's energy become visible, the colors that are shown depend upon the speed. The slower the energy, the stronger the color will be. For example, the slowest vibration is red and the fastest white.

One can also combine the meaning of the aura colors with that of the chakra colors. Chakras are the energy centers in our body. If the energy is a certain color, it means that the attention is mainly centered in a certain part of the body. For example, if one vibrates in yellow, they are sensitive in the stomach area and the third chakra is open or opens up at this time; they may also be involved yellow themes like trying to be independent.

When one's energy system malfunctions, and a part of the body stops functioning properly, it is not receiving the signals that it should and the aura will have a hole in it. Once the healing process is completed and the body healed, the aura becomes complete, where one once treated will feel good again.

Reading an aura photograph requires that it be interpreted as a whole, the combined area of it's many different parts: the shape of the aura, the energy positions and the color of the aura.

Trained therapists can restore the electrical system of the body and open up the channels of energy that runs through us. When part of our body becomes clogged or stagnant, it presents itself as pain in that area.

Figure 1A:
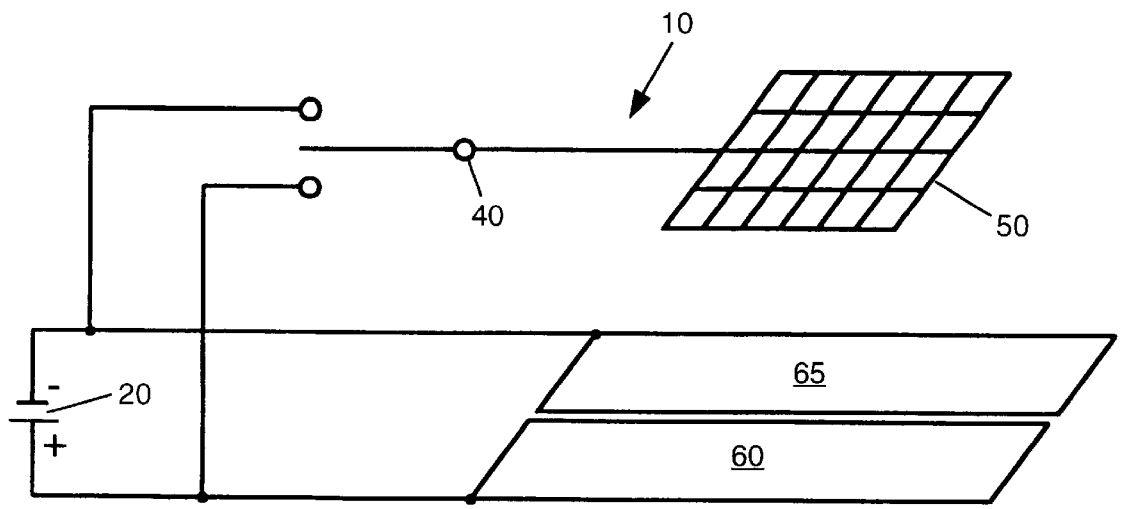
FIG. 1a is a circuit schematic for the therapeutic stimulating healing apparatus of the present invention.
Figure 1B:
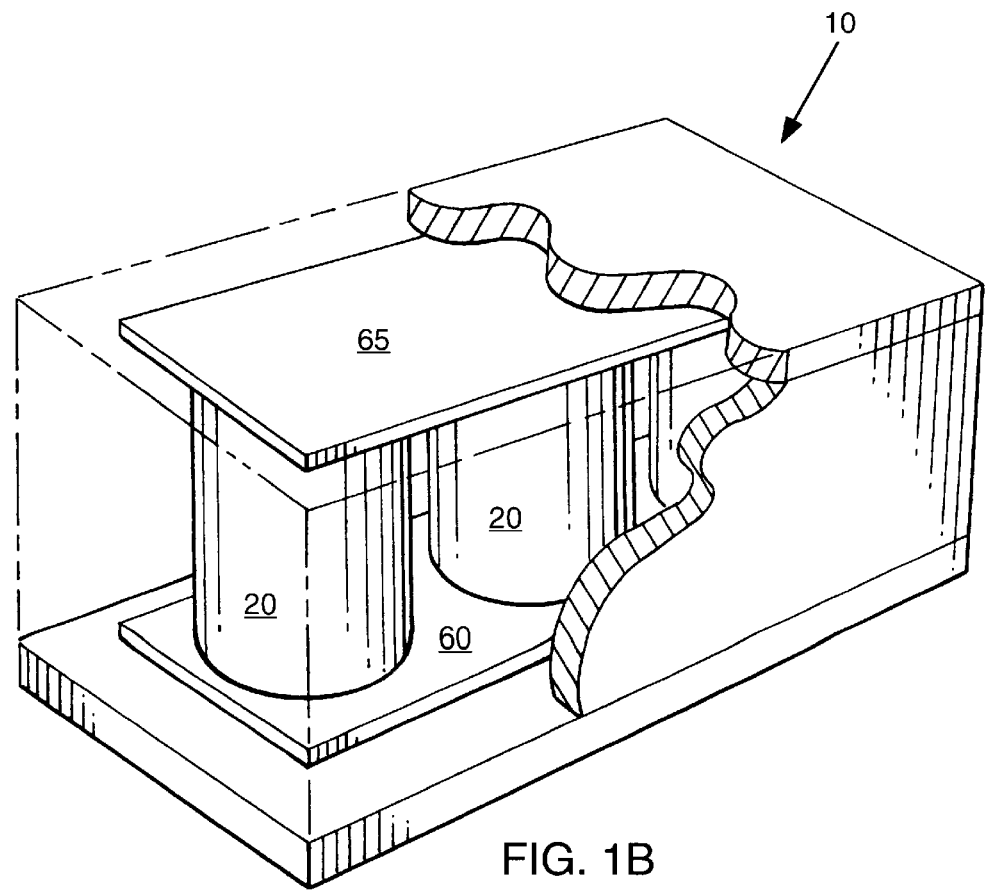
FIG. 1b is an partially cut-away perspective showing the batteries compressed between the plates.

The electrical system of one's body can be modified by stimulating the healing process using the apparatus, as shown in FIG. 1A and FIG. 1B. The present invention is comprised of two low voltage direct current sources, each having opposite polarities, the current direction being controlled by a polarity switch. A conductive wire mesh electrode is placed within a distance of 2 to 12 inches above the area to be treated.

The apparatus performs by alternately charging and discharging the cells over periods time from 1 to 12 hours. The static charge is removed by an electric discharge that resulted from the accumulation of electric charge on an insulated body. The accumulated charge manifests itself in one's aura. The healing of a malfunctioning area can be stimulated by a plurality of polarity reversals in a therapeutic application.

In a typical therapeutic session, the patient lies upon the conductive treatment surface plates 60 and 65. The conductive mesh electrode 50 is placed over the area to be treated, at a distance preferably ranging from 2 to 12 inches. The polarity switch 40 is maintained in the uppermost position for an elapsed period of approximately 15 minutes. During this interval the wire mesh 50 is connected to a negative direct current source, having a low potential. At the end of 15 minutes, the switch 40 is toggled to its lower position, connecting a positive direct current source, having a low potential to the wire mesh electrode 60, again for a period of about 15 minutes. The revered sequence is repeated several times until the therapeutic session is completed.

The placement of the electrode generally corresponds to one of the seven major areas that correspond to the chakra. The therapy, using the apparatus of the present invention, finds usefulness in soft tissue therapy; however it does not prove effective in the treatment of skeletal formations.

In the preferred embodiment, the voltage sources 20 and 30 are 10 "D" cell batteries, all connected in parallel. The voltage can range from the preferred 1.5 DC volts to about three-quarters of a volt. Treatment times can range from as little as one and one-quarter hour to as much as 12 hours of 6 hours per session.

THE USE OF THE CHAKRA IN DETERMINING PHYSICAL HEALTH

There are seven major chakras and hundreds of minor ones. In the aura the etheric, astral, and mental bodies are said to each have seven major chakras. The seven major etheric centers, which are most directly concerned with physical health, lie along the spinal column. Each is associated with a major endocrine gland, a major nerve plexus, a physiological function, and a psychic function. The higher the position along the spinal column, the more complex the chakra and the higher its functions.

The chakras are connected to each other and to the body through the nadis, channels of subtle energy. There are thousands of nadis, of which three are the most important. The "sushumna," the central channel, originates at the base of the spine and rises to the medulla oblongata at the base of the brain; it processes energy coming in from the etheric field. The "ida"and "pingala" also extend from the base of the spine to the brow and end at the left and right nostrils. They crisscross the sushumna in a spiral that resembles the shape of a caduceus. They wrap around, but do not penetrate the chakras, and are concerned with the outflow of energy.

The universal life force is said to enter the aura through the chakra at the top of the head, and is filtered down to the other chakras, each of which transforms the energy into usable form for the functions it governs. When "kundalini," the universal life force, is aroused, it rises up the chakra system through the sushumna.

Each chakra has its own coloration, number of petal "spokes," and speed of vibration. When the chakras are balanced and healthy, their colors are clear and luminous and their rotation is smooth. In poor health they become cloudy and irregular or sluggish in rotation. Chakras that are blocked are believed to adversely influence the body functions they govern. In alternative healing there are techniques for clearing chakra blockages and stimulating rotation.

The seven major etheric chakras are the root, the sacral, the solar plexus, the heart, the throat, the brow, and the crown:

1. The root (muladhara) is located at the base of the spine and is the seat of kundalini. It is concerned with self-preservation, one's animal nature, taste, and smell. It is the least complex of the seven centers, divided by only four spokes. It is red in color.

2. The sacral (svadhisthana) lies near the genitals and governs sexuality and reproduction. It has six spokes and is primarily orange. In some systems the root chakra is ascribed reproductive functions, and the sacral chakra is overlooked in favor of the spleen chakra, a rosy pink and yellow sun with six spokes located halfway between the pubis and navel. It influences overall health and in particular governs digestion and functions of the liver, pancreas, and spleen. The spleen chakra is seen as minor in other systems.

3. The solar plexus (manipura) rests just above the navel. It has ten spokes and is predominantly yellow. It is associated with the emotions, and is the point where astral energy enters the etheric field. The solar plexus affects the adrenals, pancreas, liver, and stomach. Most trance mediums work through this chakra.

4. The heart (anahata) has twelve glowing golden petals and is located midway between the shoulder blades, in the center of the chest, where the color green predominates. It governs the thymus gland and influences immunity to disease. It is linked to higher consciousness and unconditional love.

5. The throat (vishuddha) is a sixteen spoke wheel of silvery blue that is associated with creativity and self-expression and the search for truth. It is prominent in musicians, singers, composers, and public speakers. This chakra also influences the thyroid and parathyroid glands and metabolism, and is associated with certain states of expanded consciousness.

6. The brow (ajna), located between the eyebrows, is called the third eye for its influence over psychic sense and spiritual enlightenment. It has ninety-six spokes, half of which radiate a yellow-rose color and half of which radiate a violet color in blue and purple. This chakra is associated with the pituitary gland the pineal gland, intelligence intuition, and psychic powers, called siddhis in Hindu yoga.

7. The crown (sahasrara) whirls just above the top of the head. Its 972 spokes radiate a glowing white. It is not associated with any glands, but reveals the individual's level of conscious evolution. The crown cannot be activated until all the other chakras are refined and balanced; when activated it brings supreme enlightenment and cosmic consciousness. While other chakras rotate in slight depressions, the crown chakra whirls in a dome. In religious art deities saints, and mystics are portrayed with radiant crown chakras in the form of halos or domed headdresses.

Chakras—Our Energy centers

TABLE 1

| | Chakra position effect | Body position | Color | Effect by activation |
|---|---|---|---|---|
| 1 | Basis of Root Chakra Coccyx between anus and genitals Life energy | spinal column, bones, legs, intestine, blood | red | reinforce life energy sexual potence power of enforcement |
| 2 | Sacral Chakra 3 inches under navel creativity & relationship | genitals kidney, lymphatic system, digestion | orange | stimulate creativity, eroticism, appetite and digestion |
| 3 | Solar plexus Chakra 3 inches above navel wisdom | liver, stomach, gall vegetative nerve system | yellow | redeem emotions, help by depression, helps forget bad feelings |

TABLE 1-continued

| | Chakra position effect | Body position | Color | Effect by activation |
|---|---|---|---|---|
| | | | | and experiences |
| 4 | Heart Chakra middle of breast harmony and love | heart, lung circulation skin, hands | green | balances mind, body, soul, supports, love, compassion, healing |
| 5 | Throat Chakra middle of throat inspiration | voice, throat bronchial lung | blue | active communication, self expression, and independence |
| 6 | 3rd eye Chakra forehead intuition | nose, eyes, ears, face, brain | violet | stimulates mind power |
| 7 | Crown Chakra middle of the head spirituality | cranium, brain | white | activates spiritual growth, self realization |

What is claimed is:

1. A system for stimulating healing of tissue cells in a patient, comprising:

a circuit for providing intermittent low voltages of opposite polarities;

a conductive treatment surface in the circuit that contacts and supports the patient during a therapeutic application;

a conductive wire mesh electrode communicating with the circuit and adapted to be positioned an optimal distance above the tissue that is designated for treatment wherein the treatment surface comprises a pair of oppositely charged conductive plates to provide a low current electrical field for discharge of corona emanations comprising a patient's aura;

a Tesla coil and a Kirlian photography device, wherein the tissue includes an aura discharge that is visible by enhancement using the Tesla coil and Kirlian photography device, wherein the electrode position corresponds to the tissue that manifests a health disturbance in its associated aura;

and means for alternately charging and discharging the circuit to tissue cells of a patient directed to the health disturbance manifested in the aura by said Kirlian photography device.

2. The system of claim 1, wherein the means for alternately charging and discharging the circuit to tissue cells comprises a polarity switch for controlling a current direction in the circuit to stimulate healing by a plurality of polarity reversals for a plurality of intervals in a therapeutic application.

3. The system of claim 2, wherein the power source comprises a direct current source.

4. The system of claim 3, wherein the direct current source comprises a pair of batteries connected in parallel.

5. The system according to claim 4, wherein each of the batteries comprises a 10-D cell battery.

6. The system according to claim 5, wherein each interval comprises a time period of essentially 15 minutes.

7. The system according to claim 6, wherein the therapeutic application continues over a total period of from 1 to 12 hours.

8. A process for patient diagnosis to locate an area of tissue having a malady that is not readily discernible by modem diagnostics, using a Tesla coil with Kirlian photography, wherein a patient is supported on a treatment surface comprising a pair of oppositely charged conductive plates to provide a low current electrical field for discharge of corona emanations comprising the patient's aura that includes color, shape and energy positions, comprising the steps of:

a) applying an electrical field to the patient using the Tesla coil to produce the visible aura;

b) photographing the patient's aura using Kirlian photography;

c) interpreting the aura by finding areas where the aura appears incomplete; and, d) diagnosing the location of the malady in the tissue associated with the incomplete aura.

9. A process for stimulating healing of tissue by rejuvenation of cells using an apparatus that includes a circuit with a power source for providing intermittent low voltages of opposite polarities; a conductive wire mesh electrode communicating with the power source; a conductive treatment surface on the circuit that contacts and supports the patient during a therapeutic application; and, a means for alternately charging and discharging the circuit to tissue cells of a patient, comprising the steps of:

a) applying a steady state charge to the tissue that manifests a health disturbance;

b) photographing the aura of a patient to determine the area where the aura appears incomplete;

c) locating the tissue associated with the incomplete aura;

d) positioning the conductive wire mesh electrode at an optimal distance above the tissue for electrical treatment to stimulate healing;

e) reversing a polarity of the charge to the tissue for alternately charging and discharging the circuit to tissue cells of the patient and consequent acceleration of tissue healing.

* * * * *